United States Patent [19]

Wise et al.

[11] Patent Number: 5,262,127
[45] Date of Patent: Nov. 16, 1993

[54] SOLID STATE CHEMICAL MICRO-RESERVOIRS

[75] Inventors: Kensall D. Wise; Johannes W. Schwank, both of Ann Arbor; John L. Gland, Pinckney, all of Mich.

[73] Assignee: The Regents of the University of Michigan, Ann Arbor, Mich.

[21] Appl. No.: 834,199

[22] Filed: Feb. 12, 1992

[51] Int. Cl.$^5$ ............................................. G01N 27/00
[52] U.S. Cl. ......................................... 422/98; 422/88; 422/90
[58] Field of Search ................. 422/98, 90, 88, 58; 73/31.06, 31.05; 338/34; 204/425

[56] References Cited

U.S. PATENT DOCUMENTS

| | | | |
|---|---|---|---|
| 4,225,410 | 9/1980 | Pace | 422/98 |
| 4,324,761 | 4/1982 | Harris | 422/98 |
| 4,343,768 | 8/1982 | Kimura | 422/97 |
| 4,399,424 | 8/1983 | Rigby | 338/308 |
| 4,423,407 | 12/1983 | Zuckerman | 422/98 |
| 4,574,264 | 3/1986 | Takahashi et al. | 422/98 |
| 4,587,105 | 5/1986 | Bonne et al. | 422/98 |
| 4,706,493 | 11/1987 | Chang et al. | 422/98 |
| 4,772,560 | 9/1988 | Attar | 422/58 |
| 4,820,489 | 4/1989 | Rothe et al. | 422/58 |
| 4,953,387 | 9/1990 | Johnson et al. | 422/98 |

Primary Examiner—Robert J. Warden
Assistant Examiner—Hien Tran
Attorney, Agent, or Firm—Oblon, Spivak, McClelland, Maier & Neustadt

[57] ABSTRACT

The present invention relates to a method for storing chemical reagents in micro-reservoirs, a chemical sensor system and a chemical micro-reactor.

4 Claims, 2 Drawing Sheets

SOLID STATE CHEMICAL MICRO-RESERVOIRS

BACKGROUND OF THE INVENTION

1. Field of the Invention:

The invention relates to a method of storing chemical reagents.

2. Discussion of the Background:

Chemical microsensors are playing an increasingly important role in many applications where monitoring of chemical concentrations is required. Chemical microsensors have an advantage over conventional analytical technology in terms of significantly lower cost, lower power consumption, lower weight, and faster response. Chemical microsensors offer the opportunity for remote sensing, distributed realtime sensing at multiple locations, and applications requiring portable analytical instrumentation. The miniaturization of the sensor surface makes it possible to analyze extremely small amounts of sample. Typical chemical transducers encountered in chemical microsensing technology consist of thin films which undergo a rapid change in physical properties when interacting with molecules of interest.

Chemical microsensors suffer the drawbacks of deactivation, limited selectivity and limited sensitivity. The limited number of analyte/film interactions dictates both the selectivity and sensitivity for chemical microsensors. If it were possible to co-administer a co-reagent, both the selectivity and sensitivity of existing thin film sensors could be improved.

Chemical microsensor lifetime is also a problem. The exposure of the film to an analyte sometimes produces irreversible binding and "poisoning" of the surface. Chemical microsensor lifetimes could be extended by regeneration of the film surface through exposure to a reactivating chemical. It would be advantageous to both the selectivity and regeneration processes to be able to inject precise amounts of chemicals near the thin film surface.

Further, chemical microsensors need to be calibrated for quantitative analysis. A known amount of analyte must be introduced to measure the response. Some sensors are very sensitive and must be recalibrated frequently. There is presently no means for delivering micro amounts of chemical agents to a chemical sensor.

SUMMARY OF THE INVENTION

Accordingly, one object of the present invention is to provide a novel process for storing chemical reagents.

In another embodiment, the present invention relates to a chemical microsensor containing a micro-reservoir for storing chemical agents.

Another embodiment, of the present invention provides for a micro-chemical reaction system containing a plurality of micro-reservoirs.

The object of the present invention is provided for by an active thin film deposited onto at least one "window". A selected chemical is then charged onto the surface, at a certain temperature and pressure. The release of a chemical adsorbed onto or absorbed into the thin films can be triggered by rapidly increasing the temperature of the active film. In addition, these windows are equipped with electrodes for monitoring in situ the progress and end point of chemical release. The electrodes are able to monitor the electrical characteristics of the active film as it is being charged and as the chemical is being released.

BRIEF DESCRIPTION OF THE FIGURE

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
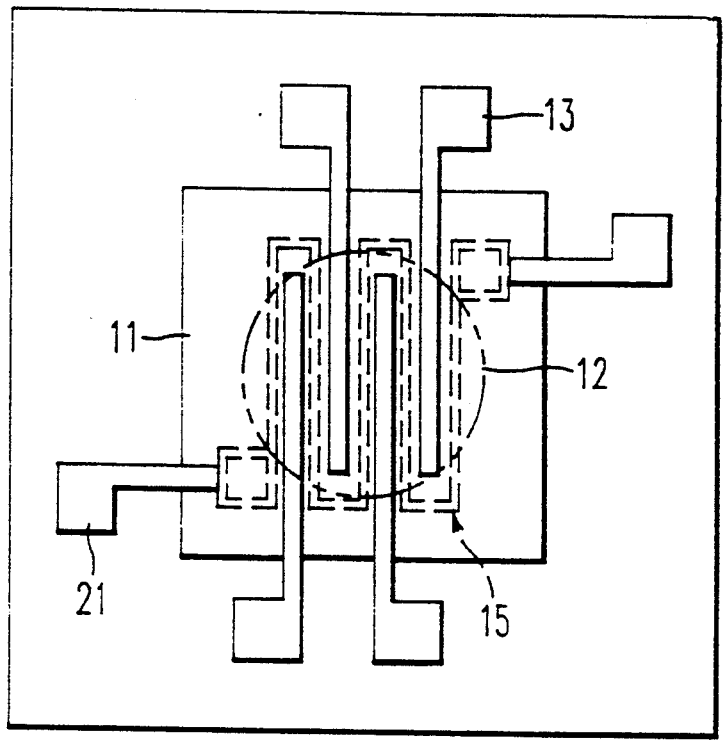
FIG. 1 provides a top view of the dielectric window used to practice the present invention.

According to the present invention, a window element is coated with an active solid film. The solid films, when charged or filled under appropriate conditions adsorb or absorb significant amounts of chemical agents, forming compounds, complexes or solutions. After charging an element at a certain temperature and pressure (for example, with hydrogen, oxygen or any other suitable reagent), the reagents can be stored for long periods of time at room temperature by the active element. Controlled release of the desired reagent is accomplished by rapidly increasing the temperature of the active film. The stored agent is then released in a controlled fashion.

The released reagents can be used as a calibration agent for chemical sensors, for reactivation or regeneration of the deactivated or poisoned sensor elements, or as reagents for enhancing the sensitivity or selectivity of sensing elements. The transport of these reagents from the storage element to the target element can be accomplished and controlled using a variety of micro-fabricated and conventional methods.

The use of stored reagents for reactivation or regeneration of deactivated or poisoned sensor elements is of substantial interest for increasing the operational lifetime and stability of a variety of chemical sensors. Stored reagents may enhance the sensitivity or selectivity of sensing elements for gases which are now difficult to detect.

Chemical micro-storage devices may also find application in micro-reactors systems for well-controlled production of small amounts of high-value added specialty chemicals, where accurate dosing of minute amounts of a given reactant is required. The stored reagents may be used to perform localized chemical reactions with great precision and reproducibility. Chemical microstorage devices may also find applications in micro-reactor systems for synthesis of small amounts of reactive chemicals which are difficult to store for extended periods.

The advantages of storing micro-reservoirs of chemical reagents is realized through a chemical sensor system containing a conventional chemical sensor and a micro-reservoir. The micro-reservoir contains a chemical reagent to be used in conjunction with the chemical sensor for such things as calibration, reactivation or selectivity/sensitivity enhancement. As a chemical sensor, conventional sensors may be used such as those described in U.S. Pat. No. 4,953,387.

Active films for micro-storage elements span the periodic table, suitable films are any film which is capable of reversibly absorbing a chemical compound. Suitable films include but are not limited to metals, metal oxides insulators, semiconductors, metal alloys, inorganic solids (i.e. hydrides, oxides, nitrides, carbides, sulfides, halides, sulfates, carbonates, intermetallic compounds and solid solutions thereof), intercalation compounds, zeolites, pillared clays, organic solids, organometallic compounds, oligomers and polymers.

The active films of the present invention include but are not limited to gold, platinum, gold-platinum, titania, titanium carbide, platinum-tin, tin oxide, titanium dioxide, zinc oxide, zirconium oxide, palladium, ruthenium, nickel, copper, rhodium, molybdenum, iridium, iron, cobalt, titanium, vanadium, tantalum, tungsten, chromium, manganese, aluminum, tin, magnesium, osmium, zinc, silver or combinations thereof.

The thickness of the thin film is from 0.5 nm to 25 nm, preferably 5 nm to 10 nm.

As chemical reagent, suitable gases include hydrogen, oxygen, $CO_2$, CO, $NO_x$, EtOH, MeOH, iPrOH, amines (such as ammonia, methylamine, ethylamine), chlorine, bromine, fluorine and iodine and chloroaromatics. Any chemical which may be reversibly bound to a chemical film then released at elevated temperature is suitable to practice the present invention.

The windows have electrodes for monitoring in situ the progress and end-point of the charging and discharging of the micro-reservoirs. The present windows are equipped with from two to four electrodes. Additional electrodes are also possible. A four-point-probe electrode configuration is capable of monitoring window impedance, which changes as a function of the absorption or release of a chemical.

The process of the present invention is practiced by exposing the array of "windows" coated with an active film to a chemical agent. The chemical agent is adsorbed onto the surface or into the bulk of the active film where it can be stored at room temperature for prolonged periods of time.

The amount of chemical reagent stored on or in a micro-reservoir may vary depending on the reagent, active film and the surface area of the film, anywhere from $10^{-5} - 10^{-3}$ mmol may be stored.

A suitable dielectric window for practicing the present process is described in U.S. Pat. No. 4,953,387. The dielectric window consists of a thin dielectric window supported by an outer rim of thicker silicon. The window is composed of successive layers of silicon dioxide, silicon nitride, and silicon dioxide which are stress compensated so as to be in mild tension. In a preferred embodiment the window forms a 1.3 mm-square by 1.3 $\mu$m-thick window. The window is successfully micromachined from a wafer bulk.

A meandering boron diffused silicon heater is located under the window which allows for heating temperatures above 1200° C. in a few milliseconds. The dielectric window provides a high degree of thermal isolation from the chip rim, ensuring high heating efficiency and low-power operation. The structure also allows for the surface of the window to be planar on its upper surface. Additional structures can be integrated onto such windows including thermocouples for independent temperature measurements, contact resistant measurement structures and different film geometries to evaluate effects of surface area on sensitivity. A rim of thick silicon provides structural stability to the device.

Figure 2:
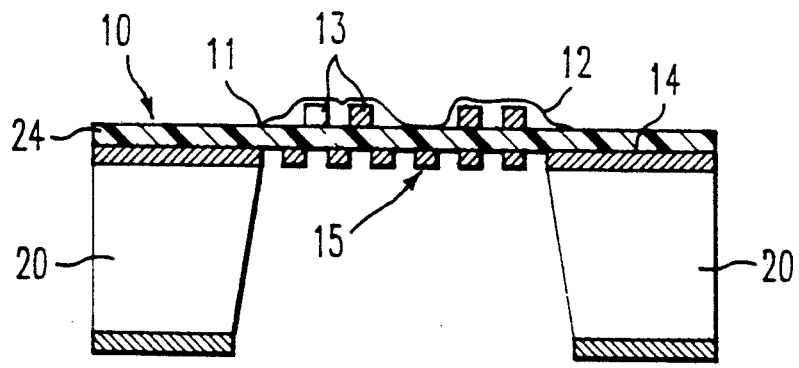
FIG. 2 provides a cross sectional view of the dielectric window used to practice the present invention.

The window is fabricated beginning with a 1175° C. solid-source boron diffusion into a patterned wafer to define the rim area of the silicon chip from the front and the pattern for defining the final window and chip size from the back. A thermal oxide is now grown, followed by polysilicon deposition, doping and patterning for the thermacouples and any other device structures. Films of low pressure chemical vapor deposition $Si_3N_4$ and $SiO_2$ complete the dielectric window stack. A buffered HF etch and an rf plasma etch are used to open contacts through the $SiO_2$ and $Si_3N_4$ to the buried heater and the thermal couple. Referring to FIGS. 1 and 2, the window features a thin-diaphragm dielectric window (11) in the center of the chip. A heater means (15) below this window allows for rapid temperature cycling of the device, in particular of the dielectric window. Heater contacts (21) are provided to the heater means (15). The substrate (24) may be advantageously designed with support means (20). The active film (12) is deposited onto the dielectric window (11) on the face opposite the heater means (15). Electrodes (13) may be provided to monitor the progress of gas absorption and release.

The substrate (24) and the dielectric window (11) of the present device comprises a $SiO_2/Si_3N_4/SiO_2$ dielectric sandwich in mild tension. The thickness of these measured as the ratio of the total thickness of silicon oxide layers to the thickness of the silicon nitride layer is greater than 1:1, preferably greater than 2.5:1, and up to 6:1.

The active film is located on the surface of the dielectric window, opposite to the heater. The active film may be deposited by a wide range of techniques for depositing films, including but not limited to sputtering, chemical vapor deposition, low pressure chemical vapor deposition-evaporation, ion beam deposition and molecular beam epitaxy. Films deposited by sputtering and chemical vapor deposition are preferred.

The present invention allows for the storage of multiple chemical agents onto different "windows" each being able to be liberated in a controlled manner. The basic device has two windows and can be abutted in a hybrid set of four chips to obtain an 8-element window array in a single package. The impedance shifts which occur when a chemical reagent is absorbed are used as indicators of chemical storage. Each window interfaces with a host node via an 8-line front end standard interface. As a result of employing this standard, each chip requires only 10 shared pads (including 3 for power and ground). Each window operates independently of each other and all can be monitored simultaneously. The circuitry designed for this device allows the temperature of each window to be set from ambient to 1200° C. with 8 bits of resolution. In order to accommodate a broad range of thin films, the on-chip inductance detector can operate on films from 3 $\Omega$ to as high as 300 K$\Omega$. Moreover, to allow the alternating current characterization of the deposited thin films, an on-chip pulse generator has been incorporated which offers 8 bits of resolution over a frequency range of from direct current to 5 MHz.

When multiple chemical reagents are stored on different windows, a chemical micro-reactor is possible. By simultaneously liberating two or more chemical reagents, a controlled chemical reaction can be conducted. Such a process is useful for preparing molecules which are difficult to store since the desired molecule can be prepared as needed.

Figure 3:
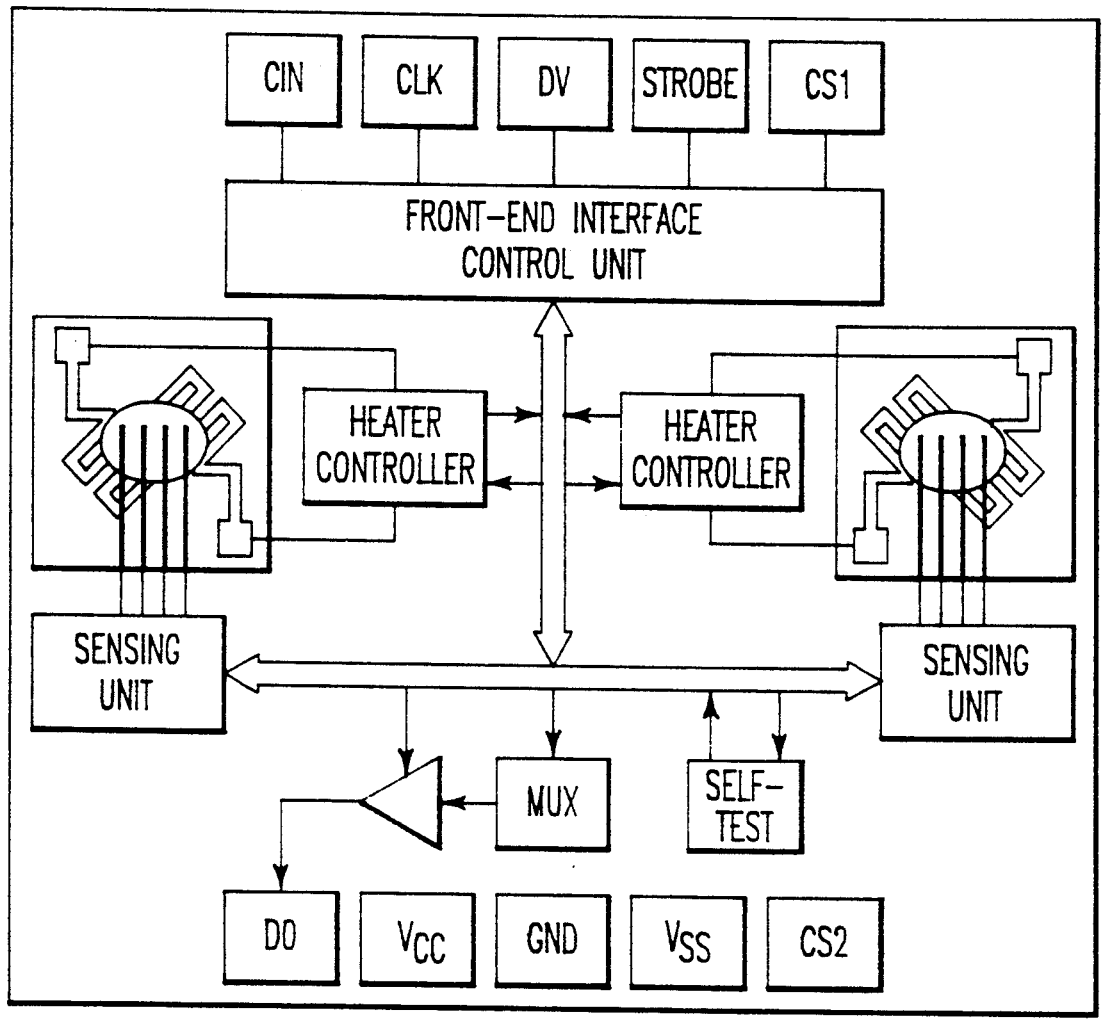
FIG. 3 provides a block diagram of a device containing multiple dielectric windows.

A block diagram of the active chip is shown in FIG. 3. The on-chip readout electronics can be divided into three major units: interface/control, heater control and sensing module. The interface/control unit is responsible for communicating with the sensor node (via the front-end standard), and for receiving, interpreting, and executing commands sent by the node. It also generates proper control signals for the other units. The heater control maintains a stable window temperature which can be programmed by the user via the front-end-standard interface. It also provides a voltage output corresponding to the window temperature which can be used to characterize the chip. Providing a stable temperature is challenging since the energy required for the heater is a function of the gas pressure and its associated thermal conductivity.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A chemical microsensing system, comprising:
   a chemical microsensor; and
   a chemical micro-reservoir comprising:
   i) a substrate comprising
      a) two opposed major surfaces including a dielectric window region;
      b) heater means situated on said dielectric window region on one side of said opposed surfaces; and
      c) a conductivity cell electrode means situated on said dielectric window on the opposite surface from said heater means;
   ii) a solid film deposited on said surface containing said conductivity cell electrode means; and
   iii) a chemical reagent absorbed onto said solid film; wherein said chemical reagent is one that is liberated from said chemical micro-reservoir and transported to said chemical microsensor.

2. A chemical micro-reactor comprising
   two micro-reservoirs, wherein each micro-reservoir comprises:
   a) two opposed major surfaces including a dielectric window region;
   b) heater means situated on said dielectric window region on one side of said opposed surfaces;
   c) an active film situated on said major surface opposed to said heater means; and
   d) a chemical reagent absorbed onto said active film; wherein said chemical reagent is different for each micro-reservoir; and wherein liberation of the two different chemical reagents results in a chemical reaction between said chemical reagents.

3. The chemical microsensing system of claim 1, further comprising at least a second chemical micro-reservoir.

4. The chemical micro-reactor of claim 2, comprising at least two micro-reservoirs.

* * * * *